(12) United States Patent
Korteweg et al.

(10) Patent No.: US 6,711,879 B2
(45) Date of Patent: Mar. 30, 2004

(54) METHOD FOR PRODUCING SURGICAL SPONGE DEVICE AND PRODUCT THEREOF

(75) Inventors: Wayne Korteweg, Ledyard, CT (US); George P. Korteweg, Mystic, CT (US)

(73) Assignee: Ultracell Medical Technologies of Connecticut, Inc., North Stonington, CT (US)

( * ) Notice: Subject to any disclaimer, the term of this patent is extended or adjusted under 35 U.S.C. 154(b) by 0 days.

(21) Appl. No.: 09/834,688

(22) Filed: Apr. 13, 2001

(65) Prior Publication Data

US 2001/0022063 A1 Sep. 20, 2001

Related U.S. Application Data

(63) Continuation-in-part of application No. 09/292,248, filed on Apr. 15, 1999, now abandoned.

(51) Int. Cl.[7] .............................................. B65B 55/22
(52) U.S. Cl. ........................................ 53/431; 53/435
(58) Field of Search .................... 53/431, 435, 513; 206/204, 210; 604/364, 1, 2, 3

(56) References Cited

U.S. PATENT DOCUMENTS

| | | |
|---|---|---|
| 2,613,862 A | 10/1952 | Vaughn |
| 3,566,871 A | 3/1971 | Richter et al. |
| 3,717,244 A | 2/1973 | Smith |
| 3,876,314 A * | 4/1975 | Nehring ...................... 604/289 |
| 3,961,629 A * | 6/1976 | Richter et al. .............. 604/369 |
| 4,098,728 A * | 7/1978 | Rosenblatt .................. 604/369 |
| 4,291,697 A | 9/1981 | Georgevich |
| 5,212,847 A * | 5/1993 | Melcher et al. ................ 604/1 |
| 5,358,480 A * | 10/1994 | Melcher et al. ................ 604/1 |
| 5,725,517 A | 3/1998 | DeBusk |
| 5,915,746 A * | 6/1999 | Melcher et al. ................ 604/1 |
| D421,302 S | 2/2000 | Korteweg |

* cited by examiner

Primary Examiner—John Sipos
Assistant Examiner—Louis Huynh
(74) Attorney, Agent, or Firm—Ira S. Dorman

(57) ABSTRACT

A surgical spear includes a cut sponge element that has been processed to render it at least substantially free from particulates and other debris; an eye spear comprised of an essentially particulate-free sponge element is uniquely suited for LASIK surgery. In most instances the surgical spear will be enclosed in a packaging component, which may or may not be fabricated from a water-permeable material and may or may not be left unsealed in the packaging step.

15 Claims, 1 Drawing Sheet

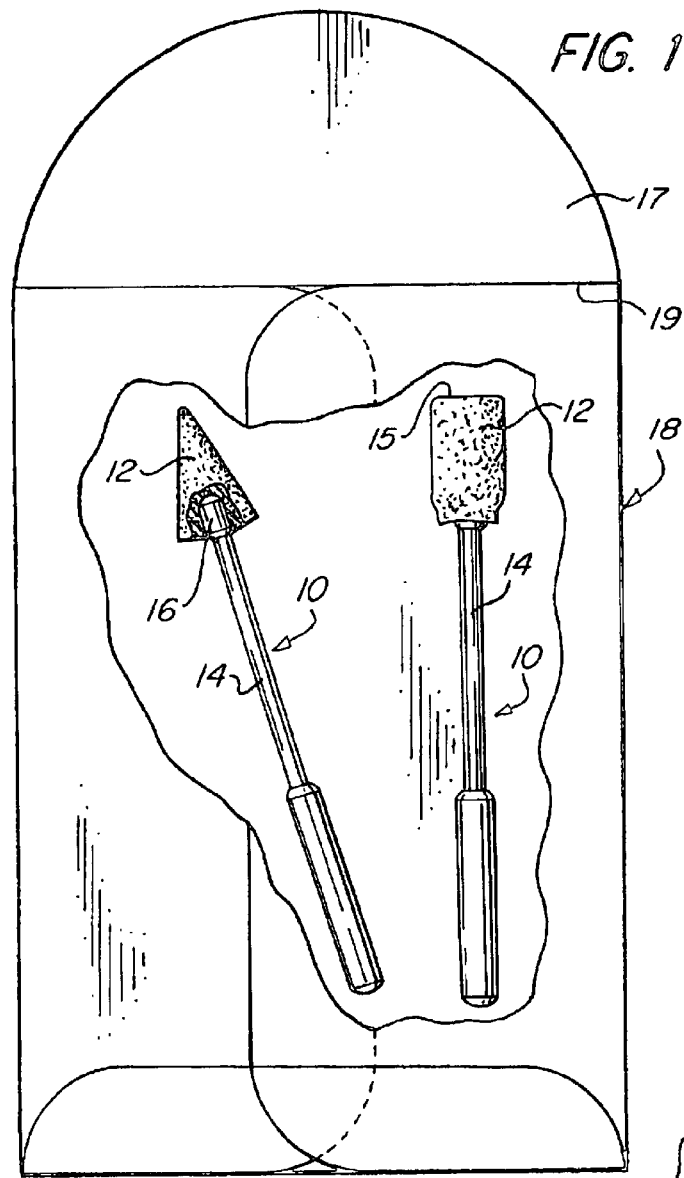

METHOD FOR PRODUCING SURGICAL SPONGE DEVICE AND PRODUCT THEREOF

CROSS-REFERENCE TO RELATED APPLICATION

This application is a continuation-in-part of copending application Ser. No. 09/292,248, filed Apr. 15, 1999 and now abandoned.

BACKGROUND OF THE INVENTION

Sponges and sponge devices are currently in widespread use for the removal and management of liquids that are produced at or introduced to a surgical site. One form of such device, called a surgical spear, is typically used in the performance of micro-surgical procedures such as eye surgery, plastic surgery, hand surgery, and the like, and will generally consist of a small sponge element to which a plastic handle is molded. Ophthalmic sponge rings are used to help keep topical anesthesia in contact with the eye during surgery, and eye drains serve to automatically and continuously wick fluid away from a surgical site; pieces of sponge sheet are used as wipes for surgical instruments and the like.

It is of course of critical importance that a surgical sponge be both sterile and also at least substantially free from foreign matter that is loose or is subject to being dislodged. Even if the sponge material does not inherently contain fragments (as is true of sponges produced from synthetic resinous materials such as, for example, polyvinyl alcohol and polyvinyl acetal), it has been appreciated that particulates are produced when a sponge is cut to a desired shape; the problem is exacerbated when a point or other small dimension is produced on the sponge element. Such sponges and sponge devices are normally furnished in protective packaging which may, in certain instances, be made of a moisture-barrier material and sealed to prevent the passage of water vapor.

The surgical spear was originally developed in the late 1960's as a device having a compressed regenerated cellulose sponge element that would rapidly remove fluids from around the eye during ophthalmic surgery. When the sponge element of the spear was brought into contact with liquid (primarily saline, used to keep the eye from drying under hot operating room lights) it would rapidly absorb and expand to its full holding capacity, whereupon it was discarded and replaced by another spear to provide a fresh, compressed sponge element.

Drawbacks inherent in the use of cellulose sponge elements include their lack of biocompatibility and a high lint and fiber content. Moreover, particulates produced during cutting become embedded in the surfaces of the compressed sponge, and are especially susceptible to being released upon expansion of the sponge during use, ultimately tending to infect the eye, particularly when encapsulated, and necessitating antibiotic treatment.

Surgical spears having polyvinyl alcohol (PVA) sponge elements were introduced in the mid- to late 1970's. It was anticipated that PVA would replace cellulose as the sponge element of choice, because the material is biocompatible, contains no inherent lint or fiber, and produces substantially less debris when cut. However, PVA sponges failed to absorb and expand as quickly as cellulose and, being much less dense than cellulose, they lacked the stiffness that is desired to enable manipulation of tissue during surgical procedures. Factors such as these caused many surgeons to continue specifying the use of cellulose spears.

Although there have been few changes in the design and construction of surgical spears in the interim, the introduction of laser surgery has given new impetus to the demand for "particulate-free" sponge material. One such procedure is laser in situ keratomileusis (LASIK) surgery, which is a modification of the original Barraquer keratomileusis procedure. The LASIK procedure is considered to be superior for correction of high myopia, and is thought to overcome many problems associated with PRK; a more rapid stabilization of refraction is achieved, and postoperative pain is reduced. Also, Bowman's layer and the epithelium are preserved at the optical axis, which seems to result in the production of almost no haze.

There are as well, however, potential problems associated with LASIK procedures, starting with the use of the microkeratome and including performing the photoablation. Additional complications include incomplete disc resection thin flap, loss of flap, or bottomholing of the flap (albeit good surgical skills and better microkeratomes can minimize them). Laser decentration, displacement, wrinkling, and edema of the flap, and lipid or epithelial deposits within the interface may also occur.

In any of event, the introduction under the cornea of lint, fibers, or other fragments larger than a certain size can cause (in addition to pervasive foreign-body concerns) refraction of light, and can thereby seriously affect the vision of the patient; consequently, the presence of such matter cannot be tolerated. Even apart from its lack of biocompatibility, these constraints virtually preclude the use of cellulose spears during LASIK surgery. And while PVA sponge elements have a much reduced inherent debris content, and indeed manufacturers have heretofore regarded them to be fiber- and lint-free, it has now been appreciated that the requisite level of purity has not been afforded, especially in respect of the demands of surgeons performing LASIK procedures.

Richter et al. U.S. Pat. No. 3,566,871 is directed to a polyurethane sponge which, albeit designed for disposability, may be washed, resterilized, and reused. In accordance with the preferred method disclosed a recirculating line is provided to remove loose pieces of foam, following which the foam body passes under infrared lamps to remove water. The dry sponge is cut into the desired size, and the resultant sponge pieces are packaged and sterilized.

Vaughn U.S. Pat. No. 2,613,862 provides a method of packaging a sponge in a wet and expanded state. DeBusk U.S. Pat. No. 5,725,517 discloses a method for making a surgical sponge from a woven web, wherein cut edges of the sponge element are folded inwardly prior to washing. Georgevich U.S. Pat. No. 4,291,697 discloses a sponge having a handle, Smith U.S. Pat. No. 3,717,244 discloses a packaged surgical sponge, and Korteweg U.S. Pat. No. D421,302 discloses a surgical spear.

SUMMARY OF THE INVENTION

The broad objects of the present invention are to provide a novel method for the production of a surgical sponge product that is at least substantially free from particulates and other debris, and to provide a novel surgical sponge product having that characteristic.

More specific objects of the invention are to provide such a method and sponge product whereby and wherein the product is enclosed in a packaging component which may desirably be fabricated from a non-barrier material and/or left in an unsealed condition.

A further specific object of the invention is to provide a surgical product, and a surgical device incorporating it, and especially a surgical spear, wherein the sponge product is sufficiently free of debris as to render it uniquely suited for use in LASIK surgery and like microsurgical procedures. Such a product will contain few if any particles that are visible at 20 power (or lower) magnification, and may be characterized as essentially particulate free.

As used herein, the phrase "sponge element" will generally refer to a piece of sponge cut from a "sponge member." The phrase "sponge product" will generally refer to a sponge element that has been processed, in accordance with the invention, to render it at least substantially particle-free, and a sponge element or product combined with another component (e.g., a handle) will generally be referred to as a "sponge device."

It has now been found that certain of the foregoing and related objects of the invention are readily attained by the provision of a method for the production of a packaged surgical sponge product, comprising the steps: providing a surgical grade sponge member; cutting the sponge member, in at least a primary cutting operation, to produce at least one sponge element defined by at least one exposed cut surface; thereafter washing the sponge element to produce a substantially particulate-free sponge element, comprising a sponge product, and packaging the sponge product in a packaging component to substantially enclose it. The method will preferably include a further step of attaching at least one handle to the sponge member prior to the primary cutting operation, ultimately to produce a sponge device comprised of the sponge product and the attached handle.

In certain embodiments the sponge product will be maintained in the expanded state subsequent to the washing step and until completion of the packaging step. The sponge product may be dried before the packaging step is carried out; it will desirably be fabricated from a material that exhibits dimensional stability in the compressed, dry state (even though it is packaged in the dry, expanded state), in which case the packaging component may advantageously be fabricated from a water vapor-permeable material and/or be left unsealed.

In other embodiments of the method a substantial amount of liquid may be maintained in the sponge product, through completion of the packaging step, with the packaging component being fabricated from a water vapor-barrier material and being sealed in the packaging step; such an amount of residual liquid will generally be that which is just sufficient to keep the sponge soft and supple. Alternatively, the sponge product may be dried and compressed subsequent to the washing step, and packaged in the same manner (but in that case, to prevent rehydration).

The cutting step of the method may include a secondary cutting operation intervening between the primary cutting operation and the washing step. In those instances in which the sponge member is fabricated from a material that exhibits dimensional stability in the compressed, dry state, the primary cutting operation will desirably be carried out with the sponge member in that state, with the secondary cutting operation being carried out with the sponge element in the expanded state. Such a method will include a further step, intervening between the primary and secondary cutting operations, of wetting the sponge element to effect its expansion; the element may or may not be recompressed subsequently.

In those embodiments in which the method includes a handle-attaching step, that step will normally be completed prior to the primary cutting operation. A multiplicity of handles may be formed simultaneously, with the primary cutting operation thereafter being performed to produce a multiplicity of sponge elements (and ultimately, sponge products) to each of which a handle is attached.

Other objects of the invention are attained by the provision of a surgical sponge product, and the corresponding packaged article, made in accordance with the method embodiments described. Sponge devices provided in accordance herewith will preferably comprise surgical spears and, in particular, spears that are especially adapted (by virtue of essential freedom from particulates) for use during ophthalmic (and particularly, LASIK) surgery.

BRIEF DESCRIPTION OF THE DRAWINGS

FIG. 1 is a plan view, partially broken away, showing two identical surgical spears embodying the present invention (in 90° axially rotated relative orientations), packaged in an unsealed glassine bag;

FIGS. 2 through 4 are side, top (or bottom), and front elevational views, respectively, of one of the surgical spears shown in FIG. 1;

FIG. 5 is a perspective view, partially broken away, showing a surgical spear embodying the invention and contained in a sealed film/foil pouch, the sponge element thereof being of modified form and in a wetted state; and FIG. 6 is a plan view showing a second form of packaged product embodying the invention.

DETAILED DESCRIPTION OF THE PREFERRED AND ILLUSTRATED EMBODIMENTS

Turning initially to FIGS. 1 through 4 of the drawing, each of the eye spears depicted, and generally designated by the numeral 1, consists of a sponge element 12 (constituting a substantially particulate-free sponge product, in accordance herewith) and an attached handle 14. Except for the area to which the head portion 16 of the handle 14 is joined, the sponge element 12 is in its expanded state. As can be seen, the sponge element 12 has a wedge-like configuration; i.e., it is of generally triangular cross section, as viewed from the top (or bottom), tapering to a leading edge 15, and is generally rectangular or fan shaped, as viewed from the side. The illustrated form of sponge element enables precise and delicate positioning for optimal removal of liquid from a surgical site, while also enabling good advantage to be taken of the inherent liquid take-up capacity of the sponge.

If the sponge element is made of PVA, or other material that is dimensionally stable in the dry, compressed state, the device depicted would typically be produced starting with a rectangular sponge member compressed to a stable, flat condition. An array of handles would be attached along opposite edges of the sponge member (normally concurrently with the production of the handles themselves, as by injection molding), after which a zigzag primary cut would be made through the member so as to produce separate spears having heads shaped as illustrated in FIGS. 1–4.

If further shaping of the sponge element is to be effected, such as to produce the element 12' on the spear 10' shown in FIG. 5, the pieces would be wetted to expand the sponge elements after making the primary cut. Opposite sides of the expanded elements would then be angularly cut (with the elements in either a wet or a dry state) to produce the pointed tip and pyramidal configuration depicted.

In all instances the device of the invention will be subjected to a washing operation subsequent to final cutting of the sponge element. Effective washing may be carried out in a machine operating in two cycles (fill/wash/rinse/spin), using either plain water or water containing a detergent or other conditioning agent. Heated water (e.g., at a temperature 100° F. to 150° F., and optimally 120° F.) will desirably be used (at least for a final rinse), preferably in combination with a detergent or other conditioning agent, to improve the effectiveness of the wash cycle, as by relaxing the sponge material and thereby promoting the release of particles. Although the washing operation may require a period of one hour or longer, it is believed that increasing the number of washing/rinsing cycles, while decreasing the period of each cycle, will enable substantial reductions in the overall washing time required. It is also believed that a procedure in which the washing liquid is recirculated through a fine filter, during the washing process, and ultimately removed from the parts in a by spin phase, would improve washing efficiency significantly.

The amount of washing liquid that is to be extracted mechanically, following the washing operation, will depend primarily upon the desired condition of the sponge preliminary to packaging. If it is to be packaged and furnished to the consumer in a "wet" state, as depicted for example in FIG. 5, the extraction phase will desirably remove no more than about 90 percent of the amount of liquid that would otherwise be retained; in such instances a degree of wetness that is just sufficient to maintain softness and suppleness will generally be optimal. If, on the other hand, the sponge is to be provided in the "dry" state, as depicted for example in FIG. 1 (which in practice means that it will usually contain about four percent of liquid, or less), mechanical means will desirably be employed to remove as much washing liquid as feasible, to thereby minimize the amount of subsequent heating necessary to dry the parts, and certainly to avoid the need for more than a single drying step.

The washed surgical sponge device will normally be inserted (individually or, more usually, together with others) into a package component such as the glassine bag depicted in FIG. 1 and generally designated by the numeral 18, the use of which represents a facile, convenient, and economical embodiment of the invention. The bag 18 would usually be closed by folding the flap portion 17 along the fold line 19, and left unsealed. If, on the other hand, the enclosure is to constitute a sealed, moisture vapor-barrier package, such as the component 20 of FIG. 5, it will typically be fabricated by peripherally heat sealing two rectangular layers of metallized MYLAR film on three sides, as at 21, and subsequently heat sealing the bottom end, as at 22, after the spear has been inserted. Other forms of enclosures can of course be employed, such as may be produced by heat sealing superimposed layers of suitable packaging materials about the device.

A number of LASIK drains 24 are shown in FIG. 6, packaged together within a fragmentarily illustrated sterile plastic bag 26, the central portion of the front wall of which is broken away. The drain 24 is fabricated entirely of sponge material, and constitutes a sponge product in accordance with the present invention; it is used in conjunction with a superior hinge or a larger corneal flap, with its ring portion serving to remove liquid before it reaches the corneal bed.

While an entire device will normally be contained therewithin, the packaging may be such that only the sponge element thereof is enclosed. As noted above, the packaging component may or may not be fabricated from a moisture vapor-barrier material, depending upon whether or not a "dry" compressed sponge element is to be maintained against hydration or, conversely, upon whether or not a "wet" sponge element is to be protected against dehydration. The sponge product may be contained in a double package, generally to ensure delivery to a sterile surgical field in uncontaminated condition; it will be appreciated however that, in such a case, only the inner package need have barrier properties and be sealed (if indeed any water vapor transmission is to be prevented).

As also noted previously, it will often be desirable that the device be delivered to the surgeon with the sponge element in compressed condition; that is done largely to accommodate the common perception that an expanded sponge is one that has already been used. On the other hand, furnishing a device having a moist, expanded element avoids the need for prewetting during the surgical procedure.

In certain instances the sponge element of the device will advantageously exhibit a degree of rigidity (when moist) sufficient to enable use by the surgeon for positioning tissue at the operating site (e.g., a corneal flap in LASIK surgery). While such rigidity is an inherent property of cellulose sponges, wetting even a small area of a compressed PVA sponge will cause the entire element to lose all rigidity. It has been found however that when only a small portion (i.e., the tip) of a PVA sponge element in a dry expanded state (made in accordance with certain embodiments of the present invention) is wetted, the element will retain sufficient rigidity to enable use for tissue manipulation.

It should perhaps be emphasized that, although the sponge element will usually be fabricated from a PVA or polyvinyl acetal resin for the reasons discussed above, other conventionally employed materials (e.g., regenerated cellulose and polyurethane) may desirably be employed in practicing the method of the invention, if so desired. For example, sponges made of materials such as polyurethane offer the advantage of being soft and supple in the dry state; indeed, it is anticipated that the availability of devices having PVA sponge elements that are packaged and delivered in dry expanded condition (as is made feasible by the instant invention) will promote a general acceptance by surgeons of non-compressed sponge devices, and thereby broaden the range of materials that can be offered successfully for use in applications of the kind described. Although one of the advantages of using a dimensionally stable compressed sponge is that doing so facilitates the production and attachment of plastic handles by conventional injection molding techniques, materials such as polyurethane can of course be locally compressed by the molding dies if the handle is to be so formed and joined.

The properties required in a surgical grade sponge material are well known to those skilled in the art and need not therefore be discussed at length. In addition to exhibiting requisite levels purity and biocompatibility, however, the material should wick at a high rate and should exhibit high liquid absorption and retention capacities. Such a sponge material will typically have a uniform distribution of open cells, the size of which may range from 0.004 mm to 1.2 mm in diameter, with an average size in the range 0.2 mm to 0.95 mm.

In producing the substantially particulate-free sponge product of the present invention, it will be appreciated that a primary objective is to eliminate those particles that would affect vision, or cause granuloma, following ophthalmic surgery; i.e. particles that would be visible under the magnification that is normally employed in performing LASIK surgery (typically, 8 to 12 power). Indicative of the ability of the present method to produce a substantially particulate-free sponge is a test (ASTM procedure F312) in which the particle content of a conventional eye spear, having a PVA sponge element with an average pore size of 0.5 mm, is compared to samples of the same product processed in accordance with the present invention. Viewed under 40-power magnification, the processed sponge elements (i.e., sponge products, in accordance herewith) were found to contain less than about 28 percent of the number of particles of 25 microns or larger that are contained in the sponge elements of conventional eye spears. Viewed at 100-power magnification, the number of particles of 10 microns or larger was reduced to less than 34 percent in the processed product, based again upon the particle content of the conventional sponges.

Further demonstrating the efficacy of the present invention are the following examples:

EXAMPLE ONE

A sheet of a commercially available surgical-grade sponge material, measuring about 8 mm thick, 375 mm long, and 140 mm wide, was compressed to about 2 mm and cut into strips about 17 mm wide and 140 mm long. Two of the strips, taken from a central area of the sheet, were die-cut into isosceles triangular shapes to produce a batch "A" of about 60 "points"(constituting the sponge elements of surgical eye spears), each point having a base about 8 mm wide and sides about 17 mm long.

The points of batch A were washed, together with two additional strips taken from the central area of the same sheet of sponge material, under conditions described hereinabove; i.e., about two hours in an automatic washing process, using water at about 50° to 70° F. (with a final rinse at about 120° F.) and containing a small amount of a conditioning agent (detergent), the water being filtered during circulation. The spin cycle of the machine used extracted most of the water, such that the samples were moist but free from water that could be removed by squeezing; all of the sample points and strips were then dried simultaneously in an oven, being maintained however separate from one another at all times to thereby avoid any possibility of cross-contamination.

The washed and dried strips were compressed and die-cut to produce about 60 additional points (batch "B") having the same dimensions as the points of batch A. All of the foregoing steps were carried out under clean, noncontaminating conditions at an FDA-inspected, ISO 9001 and EN 46001 certified facility, and the samples were carried from place to place in closed, clean plastic bags.

Five points taken from each batch were packaged in a separate plastic bag; i.e., the points from batch A were packaged together in one bag and the points from batch B were packaged together in another. An independent, EN 4501 and ISO 25 certified, testing laboratory carried out tests for the determination of particulate content in each batch, using its standard operating procedures for particulate testing of medical devices; those procedures included criteria for filter preparation, pre-counting of filters (for resident particles), cleaning of glassware, blank determination, method of counting particles, and limits for particulate matter.

More particularly, the five points from each batch being tested were placed into a beaker (one beaker being used of course for the points of batch A, and another beaker being used for the points of batch B), 100 cc of clean deionized water was injected into each beaker, and the beakers were swirled gently for one minute. In separate tests, the water was poured from each beaker into the funnel of a vacuum-operated membrane filtration apparatus fitted with a pre-counted black membrane filter having a grid-pattern surface and a pore size of 0.8 micron, and the funnel wall was rinsed with 50 cc of the deionized water while vacuum was applied.

After removal from the funnel the filter was placed upon a clean petri slide, and dried. The particles collected on each filter were counted using a calibrated microscope of at 40× and 100× power magnifications, illuminated by a high-intensity lamp.

The points from batch A were found to contain, collectively, 6,082 particles larger than 10 microns and 2,124 particles larger than 25 microns. The points from batch B were found to contain 14,452 particles larger than 10 microns and 4,035 particles larger than 25 microns.

From the foregoing it can be seen that the procedure of the invention (embodied in the batch A points) produces samples that contain only about 42 percent (i.e., about two-fifths) of the number of particles, larger than 10 microns, that is produced by the prior art technique (embodied in the batch B points), and the inventive procedure produces only about 53 percent (i.e., about half) of the number of particles larger than 25 microns.

The very substantial reductions in particulate content that are demonstrated by the foregoing Example would necessarily reduce the likelihood of contamination resulting from the use of a sponge product made in accordance herewith. A particular benefit of the method resides however in its ability to provide products, and devices comprising them, that are eminently well suited for use in LASIK surgical procedures. LASIK surgery is usually performed under 10× to 12× power magnification, and it is the particles that are visible through the microscope which are of most concern to the surgeon. At least the substantial absence of particulate debris of that size therefore constitutes a primary criterion for a sponge element or device that is optimal for use in performing LASIK surgery.

The LASIK surgeon will usually utilize an eye spear in paintbrush-like fashion, gently moving it across the corneal bed, first to clean and then to dry the surface before the corneal flap is repositioned over the bed, and finally to smooth and precisely position the returned flap. There would typically be only ten strokes of each eye spear before it is discarded.

The following example simulates the use of an eye spear in LASIK surgery.

EXAMPLE TWO

Tests were performed using a 20× power PARCO stereoscopic microscope fitted with an EMCO fiber optic light source and having a head that is mounted to pivot from side-to-side. Each test employed one eye spear produced and packaged in accordance with the method of the invention (hereinafter referred to as a "LASIK spear"), and one commercial eye spear produced in a conventional manner (hereinafter referred to as a "surgical spear"). Preliminarily, it had been determined that 20 drops of water was required to fully wet-out the sponge element of each eye spear. Using a 5 cc syringe fitted with a canula tip, two side-by-side pools were formed by depositing 30 drops (each) of distilled water into a 3-inch, clear plastic petri dish, 30 drops being used so that some water would remain after the sponge element had been saturated. The pools of water were laterally separated from one another by about one inch, and before proceeding the deposits were microscopically examined to ensure that the cleanliness of the water and petri dish had been maintained.

The LASIK spear was removed from its protective package, and its sponge element was lowered slowly into one of the pools while the surface of the pool was viewed through the microscope; the sponge absorbed the water to its full capacity in less than one second. After allowing the sponge element to reside in the water for an additional period of 10 seconds, to ensure full saturation, it was wiped gently ten times back and forth through the remaining puddle. Upon inspection, the puddle was found to contain a total of 10 to 20 particles (visible at 20× magnification).

The described procedure was repeated by introducing the sponge element of the conventional surgical spear into the other of the two pools of water deposited in the petri dish. As soon as the sponge element touched the surface it began wicking, and a flurry of particles were discharged; expansion to full capacity required about 7 to 10 seconds (such a reduced rate of wicking being typical of a compressed sponge material). Again after allowing 10 additional seconds to ensure saturation, and stroking of the sponge element through the residual water ten times, enumerable particles, of a range of sizes and shapes, were found to be present in the puddle.

More particularly, pores and cell structure could clearly be identified in the largest pieces of debris. In a midrange of particles, roughly falling into two size groups and comprising perhaps 80 to 90 percent of the debris, the particles of the larger-size group had discernable shapes and cell structure, whereas the particles of the smaller-size group appeared to be of solid form or to constitute cell-wall fragments; the smallest particles (constituting a fourth group) were similar in appearance to the smaller-size group of midrange particles.

The ability to pivot the microscope head permitted the two side-by-side pools to be compared directly. In addition to the observations already made, the particles released from the LASIK spear were seen to be similar in size to the smallest particles discharged from the conventional spear. Irrespective of source, the smallest particles appeared to be flat and two dimensional, and to float on the surface of the water; the larger particles (from the conventional spear) had descended to the bottom of the pool. It was also observed that particles had adhered to those surfaces of the petri dish which had been contacted by water during the "painting" step, thus constituting even more debris. And finally, it is noted that particles were readily visible to the naked eye in the water wiped by the conventional spear, but not by the LASIK spear.

The foregoing test was replicated five times, changing the water and petri dish for each test and utilizing fresh eye spears. All six tests produced virtually the same results, albeit in one instance a particle that would fall within the midrange of sizes described above evidently emerged from the LASIK spear.

It should be appreciated that, in contrast to the present Example, the filters utilized in Example One were inspected under 40× and 100× power magnification, and thus would obviously show far more particles than would be visible to a LASIK surgeon; indeed, even the present Example was carried out under magnification significantly more powerful than that at which LASIK surgery is normally performed. Secondly, the manner of particulate extraction employed in Example One was much more aggressive than the paintbrush-like wiping action that is used in surgical practice. And finally, the particles counted in each test of Example one represented the debris accumulated from five points whereas, as noted above, the LASIK surgeon will normally use only a single spear for each eye procedure.

Although it would seem self-evident from the foregoing detailed description, perhaps it should nevertheless be emphasized that the sequence of cutting and washing steps that are effected to produce the sponge element and product of the present method is an essential feature of the invention. No cutting step is performed subsequent to a final washing step.

Thus it can be seen that the present invention provides a novel method for the production of a surgical sponge product that is substantially free from particulates and other debris, a novel method for producing such a product enclosed in a packaging component, and novel products thereof. Surgical products, and devices incorporating them, are sufficiently free from debris as to render them uniquely suited for use in LASIK surgery and like microsurgical procedures.

Having thus described the invention, what is claimed is:

1. A method for the production of surgical sponge devices, comprising the steps:

providing a dry surgical grade sponge member fabricated from a material that exhibits dimensional stability in a compressed, dry state, and being in a compressed, flat condition;

attaching a multiplicity of handles to said sponge member in said compressed, flat condition;

cutting said sponge member, with said handles attached, in at least a primary cutting operation, to produce a multiplicity of sponge devices, each said device including a sponge element defined by at least one exposed cut surface resulting from cutting of said sponge member;

wetting said sponge devices to place said sponge elements in an expanded state; and washing said sponge devices to produce a substantially particulate-free sponge product on each said device, said washing step being carried out by subjecting said sponge devices in said expanded state to multiple washing/rinsing cycles effected in an automatic washing machine with the washing liquid being recirculated through a fine filter during said washing step.

2. The method of claim 1 wherein said cutting step includes a secondary cutting operation, intervening between said primary cutting operation and said washing step and producing a second exposed cut surface defining each of said sponge elements.

3. The method of claim 2 wherein said method includes a step of compression, to provide said sponge member in said compressed, dry state; and wherein said secondary cutting operation is carried out with said sponge elements in said expanded state.

4. The method of claim 1 wherein each of said sponge devices constitutes a surgical spear.

5. The method of claim 1 wherein said multiplicity of handles are attached to said sponge member substantially simultaneously.

6. The method of claim 1 wherein said sponge member is fabricated from a biocompatible synthetic resinous material.

7. The method of claim 6 wherein said material is polyvinyl alcohol.

8. The method of claim 1 wherein said sponge product contains virtually no particles visible under 20× power magnification or lower.

9. The method of claim 1 including the additional step of packaging said sponge devices in at least one packaging component to substantially enclose at least said sponge products.

10. The method of claim 9, wherein said sponge products are in an expanded state at least subsequent to said washing step, and are maintained in said expanded state to the completion of said packaging step.

11. The method of claim 10 including the further step of drying said sponge products, said dried, expanded sponge products being utilized in said packaging step.

12. the method of claim 11 wherein said packaging component is left unsealed in said packaging step.

13. The method of claim 11 wherein said packaging component is fabricated from a water vapor-permeable material.

14. The method of claim 10 wherein a substantial amount of liquid is maintained in said sponge products through to the completion of said packaging step, and wherein said packaging component is fabricated from a water vapor-barrier material and is sealed in said packaging step.

15. The method of claim 9 wherein said method includes the additional steps of drying, and thereafter compressing, said sponge products; wherein said dried, compressed sponge products are utilized in said packaging step; and wherein said packaging component is fabricated from a water vapor-barrier material and is sealed in said packaging step.

* * * * *